United States Patent [19]

Kreamer

[11] Patent Number: 5,758,638
[45] Date of Patent: Jun. 2, 1998

[54] INDICATOR FOR A MEDICAMENT INHALER

[76] Inventor: Jeffry W. Kreamer, 445 Blue Ash Dr., Buffalo Grove, Ill. 60089

[21] Appl. No.: 647,633

[22] Filed: May 15, 1996

Related U.S. Application Data

[63] Continuation of Ser. No. 506,223, Jul. 24, 1995, abandoned.
[51] Int. Cl.$^6$ ............................................. A61M 11/00
[52] U.S. Cl. ........................... 128/200.23; 128/200.14; 128/202.22; 128/205.23
[58] Field of Search .................. 128/200.23, 200.14, 128/202.22, 205.23

[56] References Cited

U.S. PATENT DOCUMENTS

| | | | |
|---|---|---|---|
| 4,677,975 | 7/1987 | Edgar et al. | 128/200.14 |
| 5,042,467 | 8/1991 | Foley | 128/200.23 |
| 5,062,423 | 11/1991 | Matson et al. | 128/207.15 |
| 5,284,133 | 2/1994 | Burns et al. | 128/202.22 |
| 5,363,842 | 11/1994 | Mishelevich et al. | 128/204.23 |
| 5,392,768 | 2/1995 | Johansson et al. | 128/204.23 |

FOREIGN PATENT DOCUMENTS 8802267  4/1988  WIPO .

*Primary Examiner*—V. Millin
*Assistant Examiner*—William J. Deane, Jr.
*Attorney, Agent, or Firm*—Kent A. Herink; Brian J. Laurenzo; Michael C. Gilchrist

[57] ABSTRACT

An inhaler indicator for a dispenser of an inhaled medicament, for example an asthma medicine. An inhaler body is releasably attached to the dispenser and includes a port through which air is drawn when a user of the inhaler inhales preparatory to the administration of a dose of the medicament as is required for proper administration of such medicaments. The flow of air through the port activates an audio or visual signal generator, such as a whistle or a flag, that signals to the user that the user is inhaling and that conditions are appropriate for the administration of the medicament. In an alternative embodiment, an indicator for releasable attachment to a conventional metered dose inhaler includes a passageway through which air is drawn during an inhalation of a user prepatory to the discharge of medicament. A whistle in the passageway creates an audible tone when the conditions are appropriate for discharge of the medicament. The indicator is useful as a trainer of proper technique.

9 Claims, 4 Drawing Sheets

INDICATOR FOR A MEDICAMENT INHALER

This application is a continuation-in-part application of Ser. No. 08/506,223, filed Jul. 24, 1995, now abandoned.

BACKGROUND OF THE INVENTION

The invention relates generally to medicament inhalers and, more specifically, to an indicator for use with a medicament inhaler that provides an indication to a user when the user is inhaling and conditions are appropriate for activation of the inhaler to administer a dose of the medicament.

Inhalers are in wide use for the administration of medicaments that are absorbed through the mucous membranes of the throat and lungs, such as many asthma medicines. Asthma, in particular, is becoming increasingly prevalent and more and more people are using inhalers for the administration of medicaments.

A problem with current inhalers is that they are configured to deliver the appropriate dose when the inhaler is activated during the beginning of an inhalation period of the user. Experience has shown that a great many users do not activate the inhaler at the appropriate time so that less than the full dose of the medicament is delivered to the user. Adverse results include the failure to appropriately treat the affliction and an over exposure to the medicament due to more frequent ad libitum self-administrations. Over medication can cause adverse health affects and a reduced effectiveness of the medicament than would be experienced if the correct dosage were delivered.

A number of devices have been introduced that attempt to address these problems. Such devices typically are apparatus which automatically activate the inhaler dispenser to administer a dose of the medicament when the device senses that the user is inhaling. These automatic dispensers are unnecessarily complicated and expensive. The present device offers a simple and inexpensive way to modify conventional metered dose inhalers to provide an audible signal to indicate to a user when medicament should be dispensed from the metered dose inhaler.

SUMMARY OF THE INVENTION

The invention consists of an inhaler indicator for a medicament dispenser. An inhaler body is releasably attached to the medicament dispenser at one end and includes a mouthpiece at the other end. A port is provided in the inhaler body and air is drawn through the port when a user inhales with the user's mouth over the mouthpiece. The air drawn in through the port activates an audio or visual signal generator to signal to the user that the conditions are appropriate for activation of the inhaler to administer a dose of the medicament. In the preferred embodiment, the signal generator is a whistle that produces a tone audible to the user at the beginning of an inhalation. In an alternative embodiment, the signal generator is a flag or pinwheel that is moved by a fan which is rotated in response to air being drawn through the port by an inhalation of the user.

The invention also consists of an indicator which may be added to the mouthpiece of a conventional metered dose inhaler. The indicator includes a body portion that is of a size and shape to be received in a friction fit about the mouthpiece of a conventional metered dose inhaler. The body includes a whistle in a passageway outside of the airway of the metered dose inhaler. When attached to the metered dose inhaler, the indicator produces an audible tone when the user is inhaling through the indicator at the appropriate rate for dispensing of medicament from the metered dose inhaler.

In an alternative embodiment, a separate air passageway is added to the metered dose inhaler extending from the mouthpiece opening to a port at the exterior of the metered dose inhaler. A whistle is interposed in the passageway and will produce an audible tone during an inspiration of a user when the conditions are appropriate for the dispensing of medicament from the metered dose inhaler. The passageway is separate from the interior of the metered dose inhaler and thereby provides an alternative air channel. An object of the invention is to provide a simple and inexpensive indicator for indicating to a user of a medicament inhaler that the conditions are appropriate for the administration of a dose from the inhaler.

Another object of the invention is to provide an indicator for a medicament inhaler that generates a visual or audio signal upon initiation of an inhalation by the user to indicate to the user that the inhaler should be activated.

A further object of the invention is to provide an indicator which may be attached to the mouthpiece of a conventional metered dose inhaler.

These and other objects of the invention will be made apparent to one of skill in the art upon a review of this specification, the associated drawings and the appended claims.

DETAILED DESCRIPTION OF A PREFERRED EMBODIMENT

Figure 1:
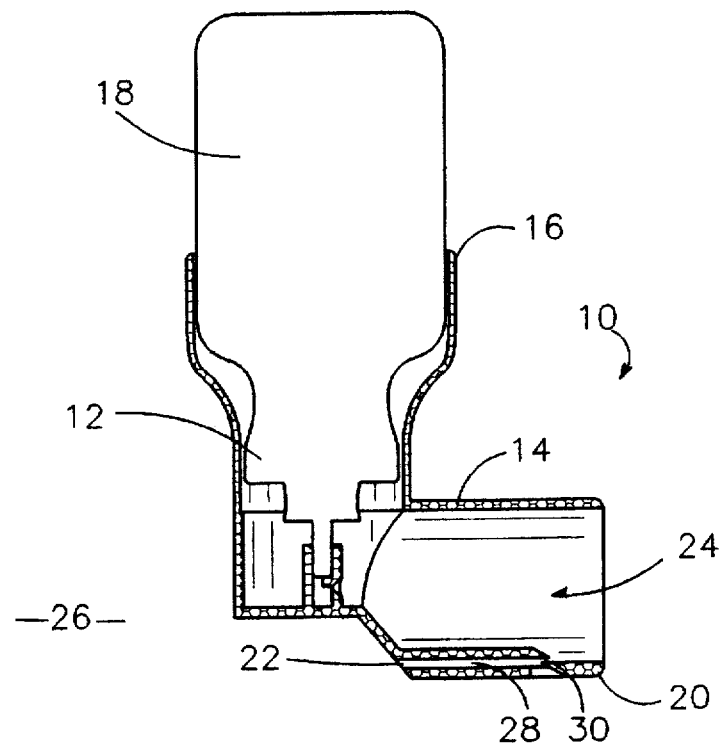
FIG. 1 is side cross sectional view of a medicament inhaler and dispenser including a whistle for generating an audio signal in response to air flow in the inhaler.
Figure 2:
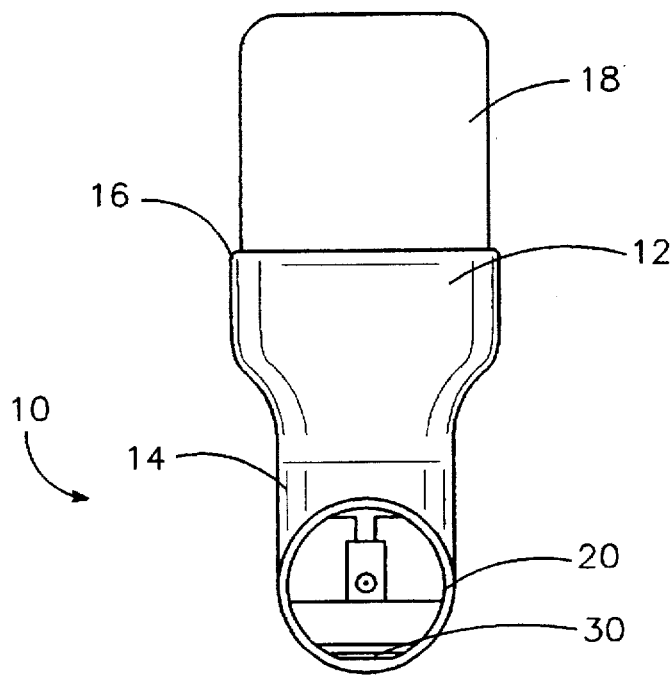
FIG. 2 is a front view of the inhaler and dispenser of FIG. 1.

Illustrated in FIGS. 1 and 2, generally at 10, is an indicator for a medicament inhaler and dispenser 12. The inhaler includes an inhaler body 14 having a base portion 16 releasably attached to a pressurized medicament dispenser 18 and a mouthpiece 20. The inhaler body 14 includes a port 22 in communication between the interior of the inhaler body 24 and the exterior of the inhaler body 26. A vacuum created at the mouthpiece 20 will act to draw ambient air from the exterior 26 to the interior of the inhaler body 24 via a passageway 28. The incoming air is directed over a whistle 30 which will produce an audible signal.

Figure 3:
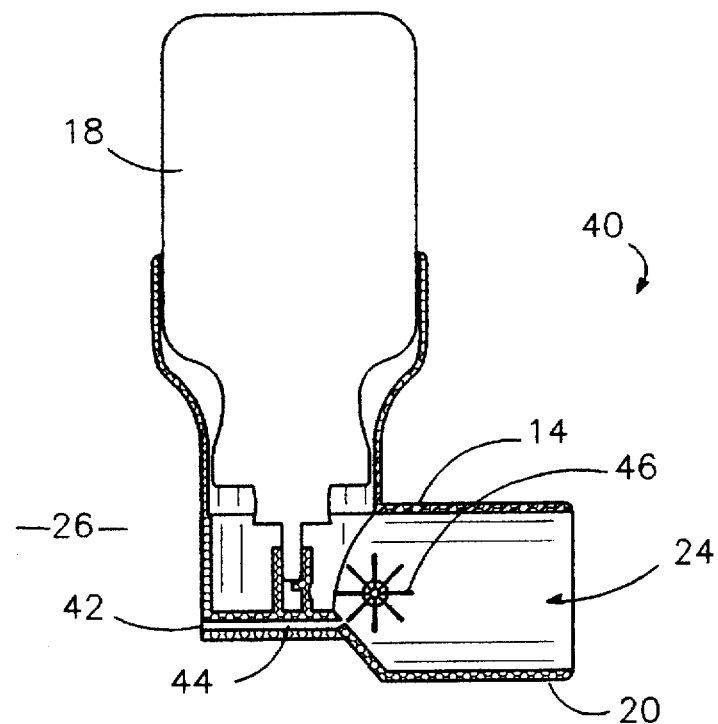
FIG. 3 is a side cross sectional view of a medicament inhaler and dispenser including a fan and rotating flag for generating a visual signal in response to air flow in the inhaler.
Figure 4:
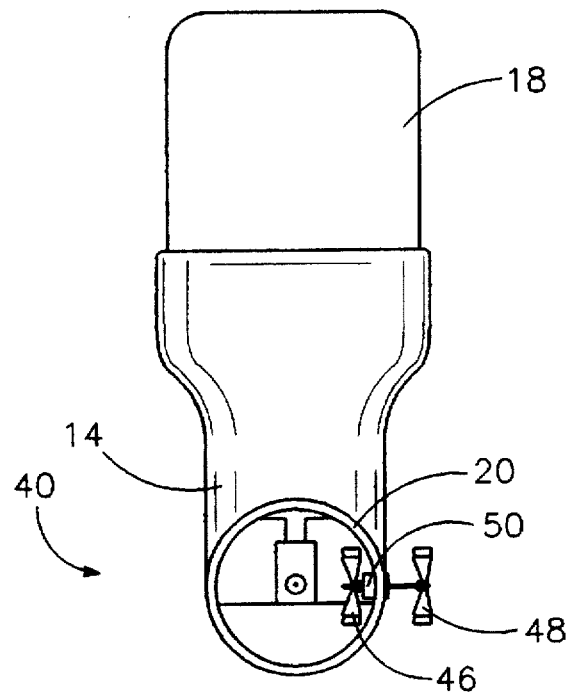
FIG. 4 is a front view of the inhaler and dispenser of FIG. 3.

An alternative indicator is illustrated in FIGS. 3 and 4, generally at 40. The inhaler body 14 includes a port 42 in communication between the interior of the inhaler body 24 and the exterior of the inhaler body 26. A vacuum created at the mouthpiece 20 will act to draw ambient air from the exterior 26 to the interior of the inhaler body 24 via a passageway 44. The incoming air is directed over a fan 46 which will rotate in response to the incoming air stream. The fan 46 is connected to a visual flag 48 exterior of the inhaler body 14 by a shaft 50 so that the flag 48 rotates with rotation of the fan 46. The flag 48 is in view of a user that has its lips enclosed about the mouthpiece 20.

Proper use of an inhaler and dispenser calls for the user to place the user's mouth over the mouthpiece 20 and substantially seal the user's lips around the mouthpiece 20. The user is then to begin an inhalation, creating a vacuum in the inhaler body 14, and then push the inhaler body 14 upwardly toward the dispenser 18. The dispenser 18 and inhaler body 14 are designed so that the inhaler body 14 slides relative to the dispenser 18 and releases a measured dose of medicament from the dispenser 18 which is then inhaled by the user. In use of the first preferred embodiment illustrated in FIGS. 1 and 2, the action of inhalation by the user will result in an audible sound being produced by the whistle 30, thereby serving as a signal to the user that an inhalation has begun and that conditions are appropriate for the administration of a dose of medicament from the inhaler and dispenser. The user will then push the inhaler body 14 upwardly to administer a dose. Similarly, in use of the second preferred embodiment illustrated in FIGS. 3 and 4, the action of inhalation will result in rotation of the flag 48 within view of the user. The user will then push the inhaler body 14 upwardly to administer a dose.

Both the whistle 30 and the flag 48 will be activated when the user is inhaling at a rate above a threshold rate of between about 0.08 and 0.18 liters per second, and preferably about 0.13 liters per second. At and above this threshold, the user is inhaling at a rate that is appropriate for the dispensing of medicament from the metered dose inhaler to achieve the delivery of the proper dose to the user. Accordingly, the user is instructed to begin inhaling and to depress the metered dose inhaler to dispense the medicament when the audible tone is first heard and to maintain a steady, uninterrupted audible tone throughout the inspiration, and then ideally to hold their breath for at least ten seconds before breathing out the nose.

Figure 5:
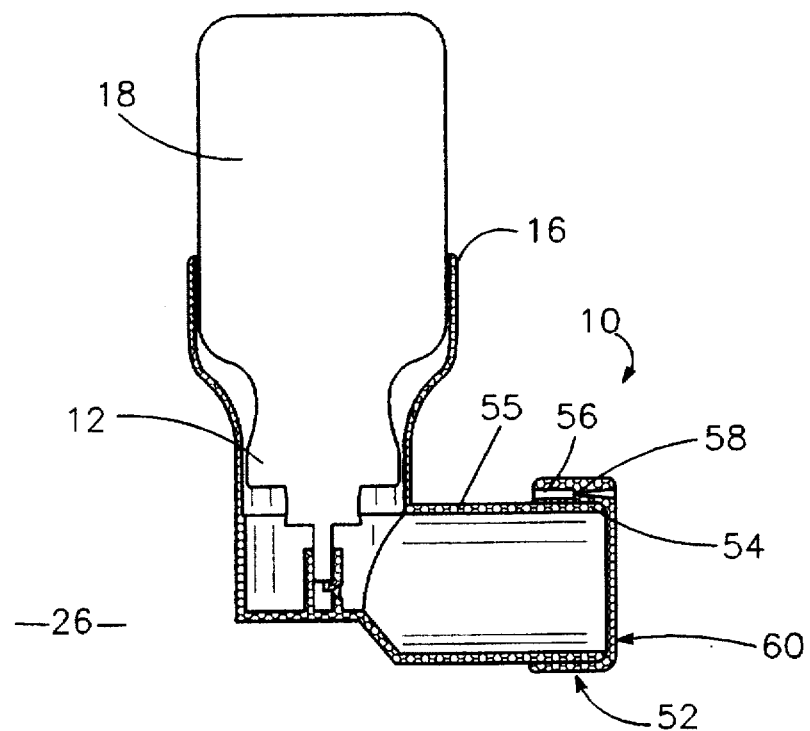
FIG. 5 is a perspective view of an indicator for attachment to the mouthpiece of a conventional metered dose inhaler.
Figure 6:
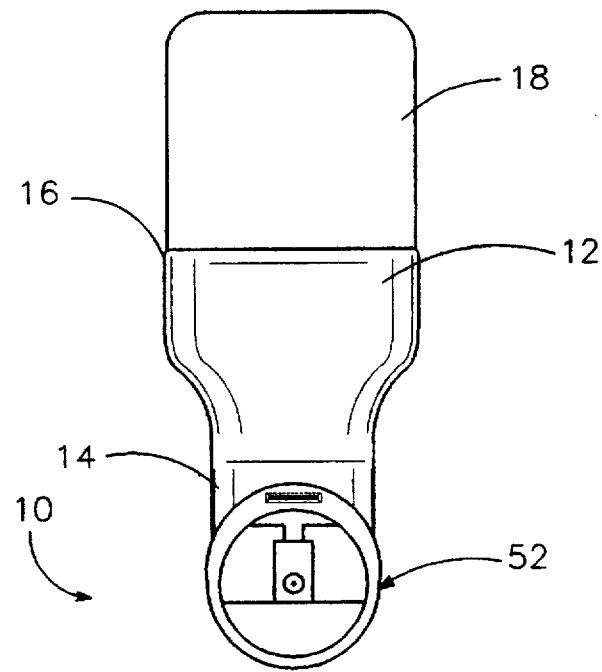
FIG. 6 is a side cross sectional view of the indicator of FIG. 5 shown attached to a metered dose inhaler.
Figure 7:
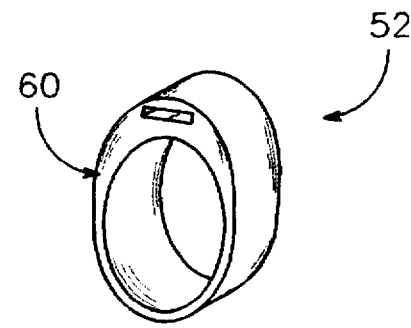
FIG. 7 is a front view of the indicator and metered dose inhaler of FIG. 6.

An indicator 52 for attachment to a conventional metered dose inhaler is illustrated in FIGS. 5–7. The indicator 52 is generally cylindrical, being of a size and shape to be received about the mouthpiece of a conventional metered dose inhaler in a friction fit so as to be releasably retained thereabout. In the preferred embodiment illustrated in FIGS. 5–7, the indicator 52 is generally circular in cross section at its inner wall so that it will fit about the mouthpiece 54 of the conventional metered dose inhaler 55 which has a circular cross section, as best illustrated in FIG. 7. Of course, the mouthpiece of the metered dose inhaler may be of an oval or other cross section, depending on the design, and the indicator will be modified accordingly to fit about the alternative shape and size.

The indicator 52 has a passageway 56 including a whistle 58. When the front end portion 60 of the indicator 52 is placed in the mouth of a user and the user's lips sealed about the front end portion 60, air will be drawn through the passageway 56 and whistle 58 during inhalation. If the rate of inhalation exceeds the threshold, an audible tone will be produced by the whistle 58. When attached to the mouthpiece of a conventional metered dose inhaler 55, as illustrated in FIGS. 6 and 7, the indicator 52 will act to indicate to a user when conditions are appropriate for dispensing of medicament from the metered dose inhaler 55. Alternatively, the indicator may be used as a training device wherein instructions are provided either in written form or orally by a medical practitioner as to appropriate use of a metered dose inhaler. The indicator can then be used to practice the proper technique.

The indicator 52 has the advantages of being small, compact and light so that it is easily transported by a user. The indicator 52 also is reusable so that it can be transferred to new metered dose inhalers as they are exhausted by the user. While the audible tone is critical to use of the indicator 52 as and indicator and trainer of proper technique, a user may use a metered dose inhaler to which the indicator 52 has been attached while eliminating the audible tone by placing a finger or the like over the intake of the passageway 56 during the inhalation. In this way, the metered dose inhaler with attached indicator 52 can be used as discreetly as an unmodified or conventional metered dose inhaler.

Figure 8:
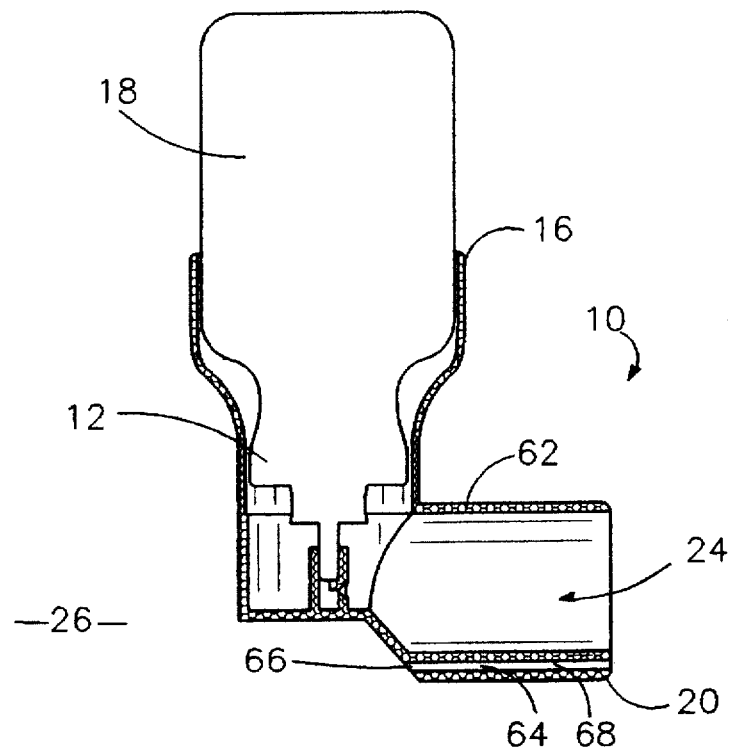
FIG. 8 is a side cross sectional view of an alternative embodiment of the indicator for the metered dose inhaler.
Figure 9:
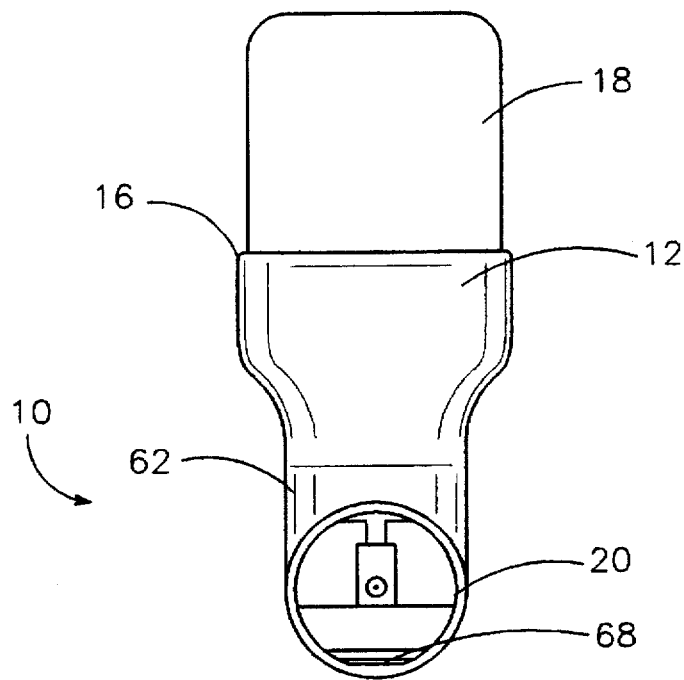
FIG. 9 is a front view of the indicator of FIG. 8.

In an alternative embodiment illustrated in FIGS. 8 and 9, the inhaler body 62 is modified by adding a passageway 64 that provides a separate air passage extending from the mouthpiece 20 rearwardly to a port 66 at the exterior of the inhaler body 62. A whistle 68 is interposed in the passageway 64 and produces an audible tone during inspiration of a user when the conditions are appropriate for dispensing of medicament from the metered dose inhaler 12. In the embodiment illustrated in FIGS. 1–4, dispensing of the medicament will cause a pressure surge inside the metered dose inhaler that will interrupt the audible tone being created by the user and which proper technique instructs to be constant or nearly so. In the embodiments of FIGS. 5–9, however, the passageway provides an independent alternative air channel so that the audible tone will not be interrupted when the medicament is dispensed. Further, the embodiments of FIGS. 5–9 allow a user to block the port at the end of the passageway to prevent the whistle from sounding without hampering the performance of the metered dose inhaler.

The invention is described as being used in association with an oral metered dose inhaler, nasal metered dose inhalers could also be adapted by the teachings of the invention to provide an audible or visual indication to a user when conditions are appropriate for dispensing of a medicament into the nasal passages of a user.

Although the invention has been described with respect to a preferred embodiment thereof, it is to be also understood that it is not to be so limited since changes and modifications can be made therein, such as the use of any variety of indicators, which are within the full intended scope of this invention as defined by the appended claims.

I claim:

1. An indicator for a metered dose inhaler which indicates to a user a condition appropriate for the discharge of a medicament from the inhaler, comprising:

(a) means for indicating to a user when conditions are appropriate for discharge of the medicament from the inhaler, said means including (i) a generally tubular indicator body having an interior and an exterior of a size and shape to be attached to said inhaler;

(ii) said indicator body including a mouthpiece for insertion into the mouth of the user and through which the medicament is dispensed to a user, said mouthpiece including a proximal edge;

(iii) a passageway in said indicator body communicating between said exterior of said indicator body and said proximal edge of said mouthpiece;

(iv) said passageway permitting ambient air to be drawn from said exterior of said indicator body to said mouthpiece and into the mouth of a user when the user is inhaling with said mouthpiece in the user's mouth; and (v) indicator means actuated by said air drawn through said passageway for indicating to a user when the user is inhaling with said mouthpiece in the user's mouth.

2. An indicator as defined in claim 1, wherein said indicator means includes audio generating means for producing a sound audible to a user in response to said air drawn through said passageway.

3. An indicator as defined in claim 2, wherein said audio generating means includes a whistle.

4. A method for administration of a medicament from a metered dose inhaler having a generally tubular indicator body having an interior and an exterior of a size and shape to be attached to said inhaler and including a mouthpiece having a proximal edge for insertion into the mouth of the user and through which the medicament is dispensed to a user, comprising the steps of:

(a) providing a passageway in said indicator body communicating between said exterior of said indicator body and the proximal edge of said mouthpiece;

(b) drawing ambient air from said exterior of said indicator body to said mouthpiece and into the mouth of a user when the user is inhaling with said mouthpiece in the user's mouth; and (c) actuating indicator means by said air drawn through said passageway for indicating to a user when the user is inhaling with said mouthpiece in the user's mouth.

5. A method as defined in claim 4, wherein said step of actuating indicator means produces an audible tone.

6. A method as described in claim 4, wherein actuating of said indicating means is continuous throughout the step of dispensing of the medicament from the dispenser.

7. An indicator for administrating a medicament from a metered dose inhaler having a generally tubular indicator body having an interior and an exterior of a size and shape to be attached to said inhaler and including a mouthpiece having a proximal edge for insertion into the mouth of the user and through which the medicament is dispensed to a user, comprising:

a) said indicator body containing a passageway communicating between said exterior of said indicator body and said proximal edge of the mouthpiece;

b) said passageway configured such that medicament and ambient air combine at said mouthpiece; and indicator means actuated by said ambient air drawn through said passageway for indicating to a user when the user is inhaling with said mouthpiece in the user's mouth.

8. An indicator as defined in claim 7, wherein actuating of said indicator means is uninterrupted by dispensing of the medicament from the dispenser.

9. An indicator as defined in claim 7, wherein said indicator means actuates when the ambient air flow through said indicator means exceeds a predetermined threshold flow rate.

* * * * *